United States Patent
Abramo et al.

(10) Patent No.: US 6,326,371 B1
(45) Date of Patent: *Dec. 4, 2001

(54) PYRUDYL AND PYRIMIDYLPIPERAZINE DERIVATIVES

(75) Inventors: Lisbeth Abramo, Bjärred; Torbjörn Lundstedt, Löddeköpinge; Curt Nordvi, Malmö ; Knut Gunnar Olsson, Malmö ; Martin Brodszki, Malmö , all of (SE)

(73) Assignee: Pharmacia Aktiebolag, Stockholm (SE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/726,362

(22) Filed: Oct. 4, 1996

Related U.S. Application Data

(63) Continuation of application No. 08/374,776, filed as application No. PCT/SE93/00632 on Jul. 16, 1993, now Pat. No. 4,652,240.

(30) Foreign Application Priority Data

Jul. 31, 1992 (SE) .................................................. 9202265

(51) Int. Cl.⁷ .................................................. A61K 31/496
(52) U.S. Cl. ................ 514/253.01; 514/218; 514/235.8; 514/253.09; 514/253.12; 514/253.13; 514/217.05; 514/252.14; 540/575; 544/121; 544/295; 544/360; 544/364; 544/365
(58) Field of Search ..................... 544/360, 364, 544/121; 514/252, 218, 235.8, 253.01, 253.12, 253.13, 253.09, 217.05; 540/575

(56) References Cited

U.S. PATENT DOCUMENTS

| | | | |
|---|---|---|---|
| 4,292,321 | 9/1981 | Pattison | 514/252 |
| 4,766,215 | 8/1988 | Abou-Gharbia et al. | 544/357 |
| 4,908,365 | 3/1990 | Buzas et al. | 514/252 |
| 4,937,245 | 6/1990 | Fex et al. | 514/252 |
| 4,994,459 | 2/1991 | Butera et al. | 514/252 |
| 4,994,460 | 2/1991 | Dextraze et al. | 514/252 |
| 5,177,078 | * 1/1993 | Ward et al. | 514/253 |
| 5,342,839 | * 8/1994 | Treiber et al. | 514/255 |
| 5,418,236 | 5/1995 | Carmosin et al. | 514/252 |
| 5,432,179 | * 7/1995 | Kumagai et al. | 514/255 |

OTHER PUBLICATIONS

Saxena,*Pharmac. Ther.* vol. 66, pp. 339–368 (1995).*

Millan et al., *Journal of Pharmacology and Experimental Theopeutics* vol. 262, p. 451–463.*

Patel et al., Indian Journal of Experimental Biology, vol. 9, No. (1), (Jan. 1971), 117–119.*

Vadodaria et al, J. Med. Chem., vol. 12, pp. 860–865(1969).

Burger, Medical Chemistry, Third Edition, Part I, pp. 74–77 (1970).

* cited by examiner

*Primary Examiner*—Emily Bernhardt
(74) *Attorney, Agent, or Firm*—Fish & Richardson P.C.

(57) ABSTRACT

The present invention relates to a method for treating a patient suffering from a mental disorder, comprising administering to the patient an effective 5-HT$_{1A}$ agonistic and 5-HT$_2$ antagonistic amount of a compound having the formula (I):

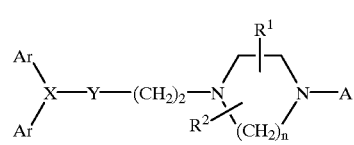

or a pharmacologically active salt thereof.

10 Claims, No Drawings

PYRUDYL AND PYRIMIDYLPIPERAZINE DERIVATIVES

CROSS-REFERENCE TO RELATED APPLICATIONS

This application is a continuation of copending application Ser. No. 08/374,776, filed on Jan. 31, 1995, the entire contents of which are hereby incorporated by reference, (now U.S. Pat. No. 4,652,240) which is a 371 of International Application No. PCT/SE93/00632 filed on Jul. 16, 1993.

BACKGROUND

There is an urgent need for efficient drugs in the treatment of mental disorders which are more effective and which have fewer side effects than the drugs in clinical use today. Antipsychotic drugs in current use produce a range of troublesome extrapyratidal movement disorders (e.g. acute dystonic reactions and tardive dyskinesia) and are poor in ameliorating the negative symptoms (e.g. restricted or blunted emotional arousal) of schizophrenia. The main disadvantage of the anti-depressants is that they fail to alleviate depression in 30 to 40% of patients. Anxioltyics are commonly associated with addictive properties.

PRIOR ART

Various pyridyl- and pyrimidyl-piperazine derivates pharmacologically active in the central nervous system are known in the art. Some representative examples can be mentioned. Azaperone, a neuroleptic drug of the butyrophenone series, is a sedative for pigs. Buspirone is an aixiolytic. The anxiolytic effect is thought to be mediated via effects on the 5HT-receptors.

Azaperone

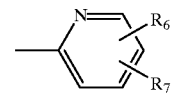

Buspirone

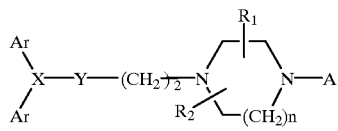

In the U.S. Pat. No. 4,937,245, compounds of the general formula C is disclosed

C

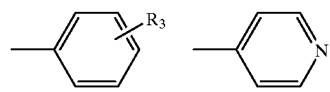

wherein A is selected from pyridyl or pyrimidyl group, e.g.

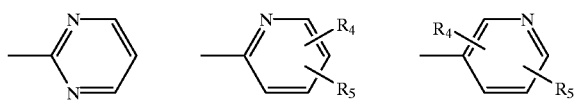

wherein preferably R6 is hydrogen and R7 is cyano, amides, methoxy or hydrogen substituent in the 3-position of the pyridyl ring, useful for the treatment of mental disorders such as psychoses, depression and anxiety.

DESCRIPTION OF THE INVENTION

According to the invention there are provided novel compounds having the general formula (I)

I

Ar\
  X—Y—(CH$_2$)$_2$—N   N—A
Ar/           R$_2$  (CH$_2$)n wherein Ar are the same or different and selected from wherein R$_3$ is fluoro or hydrogen
R$_1$ and R$_2$ are the same or different and selected from hydrogen or alkyl,
n is 2 or 3,
X is nitrogen or methane.
When X is nitrogen Y is methylene
When X is methane or carbon Y is selected from an NH group or oxygen, preferably oxygen.
A is selected from the following pyrimidyl or pyridyl derivatives.

-continued

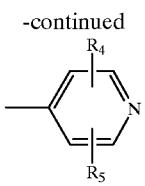

$R_4$ and $R_5$ are the same or different and selected from hydrogen, halogen, lower alkyl, electron donor groups such as lower alkoxy or hydroxy, electron acceptor groups such as cyano, nitro, trifluoromethyl, $COOR_6$, $CONR_7R_8$ or CO—B; wherein $R_6$ is hydrogen or lower alkyl; $R_7$ and $R_8$ are the same or different selected from hydrogen, lower alkyl or cycloalkyl;

B is selected from

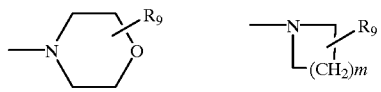

wherein m is 1, 2, 3, or 4.

$R_9$ is selected from hydrogen or lower alkyl. And the pharmacologically active salts thereof. Used in the foregoing definitions the term lower alkyl is meant to include straight and branched, saturated and unsaturated hydrocarbon groups having from 1 to 5 carbon atoms; the term cycloalkyl is meant to include cyclic, saturated and unsaturated hydrocarbon groups have from 3 to 8 carbon atoms, the term lower alkoxy is meant to include straight or branched, saturated or unsaturated alkoxy groups having from 1 to 5 carbon atoms; the term halogen is meant to include fluoro, and bromo.

The compounds of formula (I) have basic properties and, consequently, they may be converted to their therapeutically active acid addition salts by treatment with appropriated acids; e.g. inorganic acids such as hydrochloric, hydrobromic, sulfuric, nitric and phosphoric acid, or organic acids such as acetic, propanoic, glycolic, lactic, malonzi oxalic, succinic, fumaric, tartaric, citric and pamoic acid.

Conversely, the salt form can be converted into the free base form by treatment with alkali.

The compounds of formula (I) and their pharmaceutically acceptable salts have valuable pharmacological properties, making them useful for the treatment of mental disorders such as psychoses, depression and anxiety, senile dementia, Alzheimer's disease, anorexia and substance abuse disorders. Stress and anxiety in animals can also be treated.

Clinical studies have lent support to 5-hydroxytryptamine (5-HT) as being important in the pathogzenesis of mental disorders ,such as psychoses, depression, anxiety and substance abuse disorders. Considerable current activities are directed in the discovery of new psycho tropic drugs such as 5-$HT_{1A}$ agonists, e.g., buspirone and ipsapirone 5-$HT_2$ antagonists e.g. amperozide and ritanserin, 5-HT uptake inhibitors e.g. fluoxetine and paroxetine.

Since 5-$HT_{1A}$ and 5-$HT_2$ receptors have been found to interact functionally, compounds with a combined 5-$HT_{1A}$ agonistic and 5-$HT_2$ antagonistic activity would represent very interesting drugs for the treatment of patients suffering from mental disorders.

The compounds of the present invention show a high affinity for 5-$HT_1$ A and 5-$HT_2$ receptors.

While compounds of the general formula (C) and formula (I) posses high affinity for serotonin 5-$HT_{1A}$ and 5-$HT_2$ receptor subtypes, it has now quite surprisingly been found that compounds of the present invention are superior from a safety point of view, rendering them useful in therapy in the central nervous system, especially in the serotonergic system of the brain.

Effective quantities of any of the foregoing pharmacologically active compounds of formula (I) may be administrated to a human being or an animal for therapeutic purposes according to usual routes of administration and in usual forms such as solutions, emulsions, tablets, capsules and patches, in pharmaceutically acceptable carriers and parenterally, in the form of sterile solutions. Formulations for parenteral administration may be in the form of aqueous or non-aqueous isotonic sterile injection solutions or suspensions.

Although very small quantities of active materials of the present invention are effective when minor therapy is involved or in cases of administration to subjects having a relatively low body weight, unit dosages are usually from 0.5 mg upwards, depending on the condition to be treated and the age and weight of the patient as well as the response to the medication.

The unit dose may be from 0.1 to 100 milligrams, preferably from 1 to 10 milligrams. Daily doses should preferably range from 1 to 50 milligrams. The exact individual dosages as well as daily dosages will, of course be determined according to standard medical principals under the direction of a physician or veterinarian.

Methods of Preparation

The compounds having the general formula (I) may be prepared by conventional methods.

Method 1

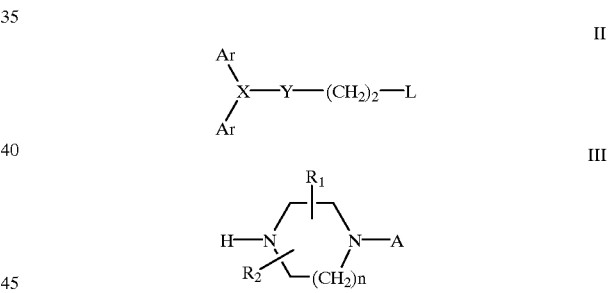

A compound of formula (II), wherein Ar, X and Y are as previously defined and L is a suitable leaving group such as halogen and alkyl- or arylsulfonate is reacted with a compound of formula (III) wherein $R_1$, $R_2$, A and n are as defined previously. The reactions may be carried out using standard N-alkylating procedures.

Method 2

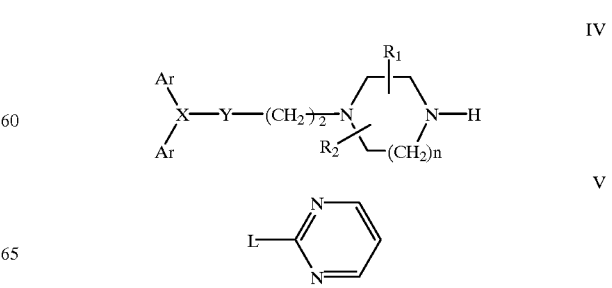

-continued

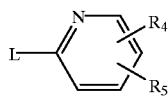

VI

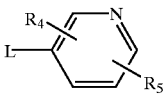

VIII

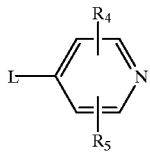

VIII

A compound of formula IV, wherein Ar, $R_1$, $R_2$, X, Y, and n are as previously defined is reacted with a compound of formula V, VI, VII, or VIII, wherein $R_4$ and $R_5$, are as previously defined and L is a suitable leaving group.

Method 3

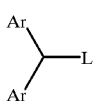

IX

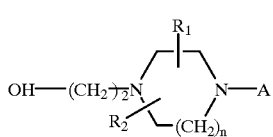

X

A compound of formula IX, wherein Ar is as previously defined is reacted with a compound of formula X, wherein $R_1$, $R_2$, n and A are as previously defined. L is hydroxy or a leaving group.

Method 4

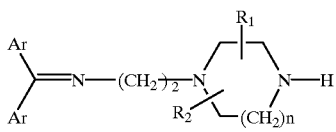

XI

A compound of formula XI wherein Ar, n, $R_1$ and $R_2$ are as previously defined is reacted with a compound of formula V, VI, VII, or VIII, to yield a product of formula XII

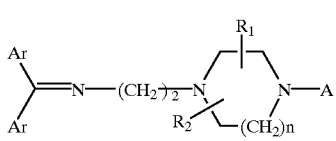

XII wherein Ar, n, $R_1$, $R_2$ and A are as previously defined. The compound XII is reduced to yield the desired product a compound of formula XIII,

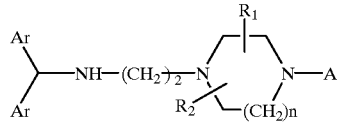

XIII

Wherein Ar, $R_1$, $R_2$, n and A are as previously defined.

EXAMPLES

The following examples are intended to illustrate but not limit the scope of the invention, although the compounds named are of particular interest for our intended purposes. These compounds have been designated by a number code, a:b, where a means the number of the example, wherein the preparation of the compound in question is described, and b refers to the order of the compounds prepared according to that example. Thus, compound 1:2 means the second compound prepared according to Example 1.

The structures of the compound are confirmed by NMR, masspectra and elementary analysis. When melting points are given, these are uncorrected.

Example 1:1

1-{3-[Bis-(4-fluorophenyl)amino]propyl}-4-(2-pyridyl)-piperazine-dihydrochloride 2.8 g (0.01 mol) of 3-[Bis-(4-p-fluorophenyl)amino]propylchloride, 3.3 g (0.02 mol) of 2-pyridylpiperazine and 0.1 g of iodine were stirred together with 20 ml of toluene at 150° C. (temperature of oil bath) for 48 h.

After cooling, the reaction mixture to ~75° C., 50 ml of toluene and 75 ml of water were added. The phases were separated and an aqueous layer was extracted three times with toluene. Evaporation of the solvents yielded the crude base which was purified by flash chromatography and isolated as an oil.

3.2 g of the free base was dissolved in 40 ml of ether. The dihydrochloride was precipitated with excess of hydrochloric acid in ethanol. Recrystallisation in 2-propanol yielded 3.2 g of the titled compound (1:1), m.p. 222–224° C.

Example 2:1

1-{3-(Bis-[4-fluorophenyl)amino]propyl}-4-(3-hydroxy-2-pyridyl)-piperazine, hydrochloride 6.6 g (0.020 mol) of 3-(N-4-Pyridyl-4-fluoroanilino) propylpiperazine, 2.8 g (0.022 mol) of 2-chloro-3-hydroxypyridine and 4.0 (0.0031 mol) of N-N-diisopropylethylamine were refluxed in xylene for 34 hr under an atmosphere of nitrogen.

After cooling, 100 ml of toluene and 100 ml of water were added to the reaction mixture The phases were separated and the aqueous layer was extracted three times with diethyl ether. Evaporation of the solvents yielded the crude base which was purified by flash chromatography and isolated. The crystals were recrystallized in ethanol:water 1:1.

3 g of the free base was dissolved in 30 ml of ethanol, ethyl acetate 1:4. The hydrochloride was precipitated with excess of hydrochloric acid in ethanol. Recrystallisation yielded 2.2 g of the titled compound (2:1), m.p. 205–207° C.

Essentially the same method was used to prepare following compounds.

2:2

1-{3-[Bis(p-fluorophenyl)amino]propyl}-4-pyrimidyl-piperazine hydrochloride m.p. 200–202° C.

2:3

1-{3-(N-4-pyridyl-4-fluoroanilino)propyl}-4-(3-carbamoyl-2-pyridyl)piperazine m.p. 120–121° C.

2:4
1-{3-(N-4-pyridyl-4-fluoroanilino)propyl}-4-(5-nitro-2-pyridyl)piperazine 1.5 hydrochloride hemihydrate m.p. 225–228° C.

2:5
1-{3-[Bis(p-fluorophenyl)amino]propyl}-4-(3-carbamoyl-2-pyridyl)piperazine dihydrochloride m.p. 226–227° C.

2:6
1-{3-[Bis(p-fluorophenyl)amino]propyl}-4-(5-nitro-2-pyridyl)piperazine hydrochloride m.p. 210–211° C.

2:7
1-{3-[Bis(p-fluorophenyl)amino]propyl)}-4-(2-(methyl-pyridine-3-carboxylate)yl)piperazine hydrochloride m.p. 181–182° C.

2:8
1-{3-[Bis(p-fluorophenyl)amino]propyl}-4-(6-chloro-2-pydyl)piperazine hydrochloride m.p. 193–194° C.

2:9
1-{2-[(4,4'-Difluorobenzhydryl)oxy]ethyl}-4-(2-(methyl-pyridine-3-carboxylate)yl)piperazine dihydrochloride m.p. 163–165° C.

2:10
1-{3-[Bis(p-fluorophenyl)amino]propyl}-4-(3—nitro-2-pyridyl)piperazine hydrochloride m.p. 170–171° C.

2:11
1-{3-[Bis(p-fluorophenyl)amino]propyl}-4-(6-fluoro-2-pyridyl)piperazine hydrochloride m.p. 190–191° C.

2:12
1-{2-[(4,4'-Difluorobenzhydryl)oxy]ethyl}-4-(6-chloro-2-pyridyl)piperazine hydrochloride m.p. 180–181° C.

Example 3:1
4-{2-[(4.4'-Difluorobenzhydryl)oxyl]ethyl}-1-(2-pyridyl) piperazine dihydrochloride 4.1 g (0.020 mol) of 1-(2-hydroxyethyl)-4-(2-pyridyl) piperazine and 2.4 g (0.010 mol) of 4-fluorobenzhydrylchloride were stirred at 165–170° C. (temperature of oil bath) for 45 min. under an atmosphere of nitrogen. After cooling, 60 ml of water and 60 ml of toluene were added to the reaction mixture. The phases were separated. Evaporation of the organic solvents yielded the crude base which was purified by flash chromatography and isolated as an oil.

2.2 g of the free base was dissolved in 40 ml of ethyl acetate. The dihydrochloride was precipitated with excess of hydrochloric acid in ethanol. Recrystallisation from isopropanol:diethylether 3:1 yielded 1.8 g of the titled compound (3:1), m.p. 167–168° C.

Example 4:1
1-{2-[(4.4'-Difluorobenzhydryl)amino]ethyl}-4-(6-chloro-2-pyridyl)piperazine 2.25 hydrochloride.

6.5 g (0.02 mol) of 1-{2-[(4,4'-Difluorobenzhydrilidene) amino]ethyl}piperazine, 3.0 g of (0.021 mol) of 2,6-dichloropyridine 3.0 g (0.025 mol) of $K_2CO_3$ and 0.1 g of iodine were stirred together with 50 ml of xylene at 140° C. for 16 h. After cooling, 100 ml of toluene was added. The solution was filtered and washed three times with water. The organic layer was dried over sodium sulphate, filtered. Evaporation of the solvent yielded 8 g of 1-{2-[(4,4'-difluorobenzhydrilidene)amino]ethyl}-4-(6-chloro-2-pyridyl)piperazine as an oil.

8 g (0.018 mol) of the oil was dissolved in 75 ml of methanol and 3.5 g (0.035 mol) of $NaBH_4$ was added and refluxed for 3 h. After cooling, 75 ml of water was added and the solvent was extracted with toluene. The organic layer was dried over sodium sulphate, filtrated and concentrated to yield 7.0 g of an oil. The hydrochloride was precipitated with hydrochloric acid in ethanol. Recrystallisation from 2-propanol yielded 5.0 g of the title compound (4:1), m.p. 235–236° C.

Essentially the same method was used to prepare following compounds.

4:2
1{[2-[(4,4'-Difluorobenzhydryl)amino]ethyl}-4-(2-(ethyl-pyridine-3-carboxylate)yl)piperazine 2.25 hydrochloride m.p. 224° C. (dec.)

4:3
1-{2-[(4,4'-Difluorobenzhydryl)amino]ethyl}-4-(3-carboxy-2-pyridyl)piperazine m.p. 229–230° C.

Example 5

This example illustrates the potency of compounds of formula (II) and their therapeutically active acid addition salts for treatment of mental disorders.

Test 1. Affinity to 5-$HT_2$ receptors.

The binding assay is carried out essentially as described by Leysen et al. (Mol. Pharmacol. 21, 301–14, 1982) using $^3$H-ketanserin as ligand.

Test 2. Affinity for 5$HT_{1A}$-receptors.

The binding assay was carried out essentially as described by Peroutka S. J., (Brain Res. 344, 167–171, 1985).

TABLE 1

Affinity to 5-$HT_2$ receptors.

| Compound | $K_i$ (nM) |
|---|---|
| 3:1 | 11 |
| 1:1 | 18 |

TABLE 2

Affinity for 5$HT_{1A}$-receptors.

| Compound | $K_i$ (nM) |
|---|---|
| 1:1 | 1.7 |

Example 6

The following formulations are representative for all of the pharmacologically active compounds of this invention. Example of a suitable capsule formulation:

| | Per capsule, mg |
|---|---|
| Active ingredient, as salt | 10 |
| Lactose | 250 |

-continued

| | Per capsule, mg |
|---|---|
| Starch | 120 |
| Magnesium stearate | 5 |
| Total | 385 |

In case of higher amounts of active ingredients, the amount of lactose used may be reduced.

Example of a suitable tablet formulation.

| | Per tablet, mg |
|---|---|
| active ingredient, as salt | 10 |
| Potato starch | 90 |
| Collodial Silica | 10 |
| Talc | 20 |
| Magnesium stearate | 2 |
| 5% aqueous solution of gelatine | 25 |
| Total | 157 |

Solutions for parenteral applications by injection can be prepared in a aqueous solution of a water-soluble pharmaceutically acceptable salt of the active substance preferably in a concentration of from about 0.5% to about 5% by weight. These solutions may also contain stabilizing agents and/or buffering agents and may conveniently be provided in various dosage unit ampoules.

What is claimed is:

1. A method for treating a patient suffering from a mental disorder, which comprises:

administering to said patient an effective 5-HT$_{1A}$ agonistic and 5-HT$_2$ antagonistic amount of a compound having the formula (I)

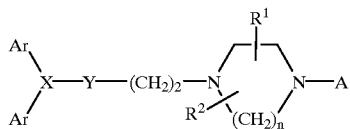

(I)

wherein

Ar is

$R_1$ and $R_2$ are each the same or different and are selected from hydrogen or lower alkyl;
n is 2 or 3;
X is methane;
Y is oxygen;
A is selected from the following substituted or unsubstituted pyridyl groups

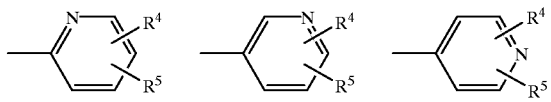

wherein
$R_4$ and $R_5$ are each the same or different and are selected from hydrogen, halogen, lower alkyl, an electron donor group selected from the group consisting of a lower alkoxy group and a hydroxy group, and an electron acceptor group selected from the group consisting of cyano, nitro, trifluoromethyl, COOR$^6$, CONR$^7$R$^8$ and CO—B, wherein
$R^6$ is hydrogen or lower alkyl,
$R^7$ and $R^8$ are each the same or different and are selected from hydrogen, lower alkyl or cycloalkyl, and
B is

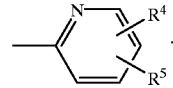   , wherein m is 1,2,3 or 4, and
$R^9$ is hydrogen or lower alkyl;
or a pharmacologically active salt thereof,
wherein said mental disorder is at least one selected from the group consisting of a psychoses, depression, and anxiety.

2. The method of claim 1, wherein n is 2.
3. The method of claim 1 or 2, wherein $R_1$ and $R_2$ are hydrogen.
4. The method of claim 3, wherein A is

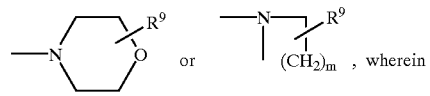

5. The method of claim 1, wherein said electron donor group is a lower alkoxy or hydroxy group, said electron acceptor group is a cyano, nitro, trifluoromethyl, COOR$^6$ CONR$^7$R$^8$ or CO—B;

wherein R$^6$ is hydrogen or lower alkyl, R$^7$ and R$^8$ are each the same or different and are selected from hydrogen, lower alkyl or cycloalkyl; and B is

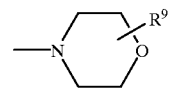

wherein R$^9$ is selected from hydrogen or lower alkyl.
6. The method of claim 1, wherein said compound is 4-{2-[(4,4'-difluorobenzhydryl)-oxy]ethyl}-1-(2-pyridyl)piperazine or a pharmacologically acceptable salt thereof.
7. The method of claim 6, wherein said 4-{2-[(4,4'-difluorobenzhydryl)oxy]ethyl}-1-(2-pyridyl)piperazine compound is the dihydrochloride salt thereof.
8. The method of claim 1, wherein said mental disorder is a psychoses.
9. The method of claim 1, wherein said mental disorder is depression.
10. The method of claim 1, wherein said mental disorder is anxiety.

* * * * *